United States Patent
Johnson

(10) Patent No.: US 11,056,217 B2
(45) Date of Patent: *Jul. 6, 2021

(54) SYSTEMS AND METHODS FOR FACILITATING HEALTH RESEARCH USING A PERSONAL WEARABLE DEVICE WITH RESEARCH MODE

(71) Applicant: Apple Inc., Cupertino, CA (US)

(72) Inventor: Timothy M. Johnson, San Jose, CA (US)

(73) Assignee: Apple Inc., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/590,131

(22) Filed: Oct. 1, 2019

(65) Prior Publication Data
US 2020/0105382 A1    Apr. 2, 2020

Related U.S. Application Data

(63) Continuation of application No. 15/988,927, filed on May 24, 2018, now Pat. No. 10,460,834, which is a
(Continued)

(51) Int. Cl.
*G16H 10/20* (2018.01)
*G16H 50/70* (2018.01)
(Continued)

(52) U.S. Cl.
CPC ............. *G16H 10/20* (2018.01); *G16H 10/60* (2018.01); *G16H 40/63* (2018.01); *G16H 40/67* (2018.01);
(Continued)

(58) Field of Classification Search
None
See application file for complete search history.

(56) References Cited

U.S. PATENT DOCUMENTS 3,972,320 A    8/1976 Kalman
6,820,057 B1   11/2004 Loch et al.
(Continued)

FOREIGN PATENT DOCUMENTS

CN    1395214      2/2003
CN    101286169    10/2008
(Continued)

OTHER PUBLICATIONS

Beresford et al., "Mockdroid: Trading Privacy for Application Functionality on Smartphones", Proceedings of the 12th Workshop on Mobile Computing Systems and Applications, HotMobile '11, New York, Jan. 1, 2011, 6 pages.
(Continued)

*Primary Examiner* — Curtis A Kuntz
*Assistant Examiner* — Jerold B Murphy
(74) *Attorney, Agent, or Firm* — Kilpatrick Townsend & Stockton LLP

(57) ABSTRACT

Methods and systems for facilitating health research by utilizing one or more wearable sensor devices with a research mode are provided herein. Systems include a wearable sensor device that can pair with a first portable computing device of a user and a second computing device of a researcher in a first and second pairing, respectively. The wearable sensor device obtains one or more health parameters of a user. In one aspect, the wearable sensor device communicates research related and non-research related health information to the first computing device via the first pairing link and communicates only research related health information to the second computing device via the second pairing link. Methods for pairing one or more wearable sensor devices with one or more research computing devices and switching between operating modes to provide additional research related features are also provided.

20 Claims, 11 Drawing Sheets

Related U.S. Application Data continuation of application No. 15/089,246, filed on Apr. 1, 2016, now Pat. No. 9,996,678.

(60) Provisional application No. 62/235,210, filed on Sep. 30, 2015.

(51) Int. Cl.
| | |
|---|---|
| *G16H 40/63* | (2018.01) |
| *G16H 10/60* | (2018.01) |
| *H04W 4/80* | (2018.01) |
| *H04W 76/10* | (2018.01) |
| *H04W 76/11* | (2018.01) |
| *G16H 40/67* | (2018.01) |
| *H04W 84/18* | (2009.01) |

(52) U.S. Cl.
CPC .............. *G16H 50/70* (2018.01); *H04W 4/80* (2018.02); *H04W 76/10* (2018.02); *H04W 76/11* (2018.02); *H04W 84/18* (2013.01)

(56) References Cited

U.S. PATENT DOCUMENTS

| | | | |
|---|---|---|---|
| 7,038,595 B2 | 5/2006 | Seely | |
| 7,515,044 B2 | 4/2009 | Welch et al. | |
| 8,005,691 B2 | 8/2011 | Kumar et al. | |
| 8,063,776 B2 | 11/2011 | Ruha | |
| 8,157,730 B2 | 4/2012 | Leboeuf et al. | |
| 8,190,651 B2 | 5/2012 | Treu et al. | |
| 8,423,387 B1 | 4/2013 | Mirza | |
| 8,715,181 B2 | 5/2014 | Brynelsen et al. | |
| 8,737,971 B2 | 5/2014 | Van Rooyen et al. | |
| 8,817,642 B2 | 8/2014 | Donaldson | |
| 8,818,823 B2 | 8/2014 | Ackerson et al. | |
| 8,839,389 B2 | 9/2014 | Cohen et al. | |
| 8,930,221 B2 | 1/2015 | Ackerson et al. | |
| 8,976,007 B2 | 3/2015 | Dugan et al. | |
| 9,014,779 B2 | 4/2015 | Zdeblick et al. | |
| 9,031,581 B1 | 5/2015 | Haney et al. | |
| 9,058,503 B2 | 6/2015 | Bernaudin et al. | |
| 9,069,333 B1 | 6/2015 | Romans | |
| 9,582,642 B2 | 2/2017 | Keen et al. | |
| 9,996,678 B2 * | 6/2018 | Johnson .................. | G16H 50/70 |
| 10,236,079 B2 | 3/2019 | Keen | |
| 10,290,367 B2 | 5/2019 | Keen et al. | |
| 10,460,834 B2 * | 10/2019 | Johnson .................. | G16H 10/20 |
| 2001/0032100 A1 | 10/2001 | Mahmud et al. | |
| 2001/0034617 A1 | 10/2001 | Kimata | |
| 2002/0005935 A1 | 1/2002 | Robin | |
| 2003/0028400 A1 | 2/2003 | Christ et al. | |
| 2003/0074221 A1 | 4/2003 | Christ et al. | |
| 2003/0088520 A1 | 5/2003 | Bohrer et al. | |
| 2004/0054760 A1 | 3/2004 | Ewing et al. | |
| 2005/0049898 A1 | 3/2005 | Hirakawa | |
| 2006/0248592 A1 | 11/2006 | Agrawal et al. | |
| 2006/0248593 A1 | 11/2006 | Dennis et al. | |
| 2008/0104615 A1 | 5/2008 | Nolan et al. | |
| 2008/0133639 A1 | 6/2008 | Panasyuk et al. | |
| 2008/0162352 A1 | 7/2008 | Gizewski | |
| 2009/0076349 A1 | 3/2009 | Libbus et al. | |
| 2009/0320096 A1 | 12/2009 | Nolan et al. | |
| 2010/0081890 A1 | 4/2010 | Li et al. | |
| 2010/0306827 A1 | 12/2010 | Esteve Balducci et al. | |
| 2011/0295616 A1 | 12/2011 | Vesto | |
| 2012/0101847 A1 | 4/2012 | Johnson et al. | |
| 2012/0313776 A1 | 12/2012 | Utter, II | |
| 2013/0030836 A1 | 1/2013 | Ackerson et al. | |
| 2013/0053655 A1 | 2/2013 | Castellanos | |
| 2013/0064358 A1 | 3/2013 | Nusbaum | |
| 2013/0106684 A1 | 5/2013 | Weast et al. | |
| 2013/0197942 A1 | 8/2013 | Chiu et al. | |
| 2013/0231947 A1 | 9/2013 | Shusterman | |
| 2013/0268641 A1 | 10/2013 | Colbert et al. | |
| 2013/0275151 A1 | 10/2013 | Moore et al. | |
| 2013/0304511 A1 | 11/2013 | Gunter | |
| 2014/0018048 A1 | 1/2014 | Anand et al. | |
| 2014/0059695 A1 | 2/2014 | Parecki et al. | |
| 2014/0081662 A1 | 3/2014 | Bradrick et al. | |
| 2014/0118159 A1 | 5/2014 | Fish et al. | |
| 2014/0122125 A1 | 5/2014 | Deshpande et al. | |
| 2014/0135592 A1 | 5/2014 | Ohnemus et al. | |
| 2014/0197947 A1 | 7/2014 | Bahorich | |
| 2014/0242698 A1 | 8/2014 | Smith | |
| 2014/0247155 A1 | 9/2014 | Proud | |
| 2014/0257851 A1 | 9/2014 | Walker et al. | |
| 2014/0257854 A1 | 9/2014 | Becker et al. | |
| 2014/0276552 A1 | 9/2014 | Nguyen et al. | |
| 2014/0278474 A1 | 9/2014 | McClure et al. | |
| 2014/0297320 A1 | 10/2014 | Jiwani et al. | |
| 2014/0324469 A1 | 10/2014 | Reiner | |
| 2015/0025401 A1 | 1/2015 | Wright | |
| 2015/0094544 A1 | 4/2015 | Spolin et al. | |
| 2015/0173674 A1 | 6/2015 | Hayes et al. | |
| 2015/0182128 A1 | 7/2015 | Magi | |
| 2015/0199424 A1 | 7/2015 | Damodaran et al. | |
| 2015/0223705 A1 | 8/2015 | Sadhu | |
| 2015/0242592 A1 | 8/2015 | Weiss et al. | |
| 2015/0244852 A1 | 8/2015 | Erickson et al. | |
| 2015/0289820 A1 | 10/2015 | Miller et al. | |
| 2015/0294090 A1 | 10/2015 | Kodiyan et al. | |
| 2015/0310174 A1 | 10/2015 | Coudert et al. | |
| 2015/0347499 A1 | 12/2015 | Keen et al. | |
| 2015/0347684 A1 | 12/2015 | Keen et al. | |
| 2015/0347690 A1 | 12/2015 | Keen et al. | |
| 2015/0347784 A1 | 12/2015 | Keen | |
| 2016/0029177 A1 | 1/2016 | Park et al. | |
| 2016/0048695 A1 | 2/2016 | Cucinotta | |
| 2016/0066184 A1 | 3/2016 | Bhargav-Spantzel | |
| 2016/0210416 A1 | 7/2016 | Whitehurst | |
| 2016/0267238 A1 | 9/2016 | Nag | |
| 2016/0301792 A1 | 10/2016 | Lee et al. | |
| 2017/0011182 A1 | 1/2017 | Whitehurst | |
| 2017/0091412 A1 | 3/2017 | Johnson | |

FOREIGN PATENT DOCUMENTS

| | | |
|---|---|---|
| CN | 101393520 | 3/2009 |
| CN | 101667224 | 3/2010 |
| CN | 103182175 | 7/2013 |
| CN | 103278752 | 9/2013 |
| WO | 2013152189 | 10/2013 |
| WO | 2015183495 | 12/2015 |

OTHER PUBLICATIONS

Hornyack et al., "These Aren't the Droids You're Looking for: Retrofitting Android to Protect Data from Imperious Application", Computer and Communications Security, ACM, 2, Oct. 17, 2011, pp. 639-651.

Zhou et al., "Taming Information-Stealing Smartphone Applications on Android", Department of Computer Science, NC State University, Huawei American Research Center, Jan. 1, 2011, 15 pages.

* cited by examiner

SYSTEMS AND METHODS FOR FACILITATING HEALTH RESEARCH USING A PERSONAL WEARABLE DEVICE WITH RESEARCH MODE

CROSS REFERENCES TO RELATED APPLICATIONS

The present application is a Continuation of U.S. patent application Ser. No. 15/988,927 filed May 24, 2018 (Allowed); which is a Continuation of U.S. patent application Ser. No. 15/089,246 filed Apr. 1, 2016 (now U.S. Pat. No. 9,996,678); which claims the benefit of U.S. Provisional Appln. No. 62/235,210 filed Sep. 30, 2015; the full disclosures which are incorporated herein by reference in their entirety for all purposes.

The present application is related to U.S. Provisional Appln. No. 62/006,031 filed May 30, 2014, entitled "Managing User Information Authorization Masking"; and U.S. Provisional Appln. No. 62/129,691 filed Mar. 6, 2015, entitled "Systems and Methods for Facilitating Health Research;" the entire contents of each are hereby incorporated by reference for all purposes.

FIELD OF INVENTION

The present invention relates to systems and methods for facilitating health research through enhanced communication of health information between research participants and researchers. In particular, the invention relates systems and methods for facilitating health research by utilizing wearable sensor devices.

BACKGROUND OF THE INVENTION

Traditionally, health research studies involve gathering and exchange of health data from one or more health research participants. Gathering data from research participants can be a complex and invasive process, particularly when a study involves multiple research participants. While monitoring devices and methods of collection exist, such devices are often costly and of limited usefulness as such devices often lack advanced capabilities and communication and are not readily compatible with standard computing devices.

These challenges often undesirably limit the amount and frequency of health data collection in a research study as well as limit the number of participants that can reasonably be included in a research study. Therefore, there exists a need to provide a system that utilizes wearable devices that offers more robust, advanced capabilities while providing functionality for use within a research study by multiple researchers. Providing these improvements is challenging and often problematic given the limited time and resources available in modern healthcare in addition to heightened concerns as to user privacy.

BRIEF SUMMARY OF THE INVENTION

Methods of the present invention pertain to facilitating research by improved communication between the researchers and research participants. In one aspect, the system includes an application framework on a portable computing device of a research participant that performs various research objectives using one or more modules received within the framework.

In one aspect, a system for facilitating research in accordance with embodiments of the invention includes a wearable sensor device. The wearable sensor device includes one or more sensors adapted to detect one or more health parameters of the user when worn and a user interface for presenting the one or more health parameters to the user. The device further includes a wireless communication unit adapted to for pairing and local communication with multiple companion computing devices. In some embodiments, initial pairing is performed using NFC and subsequent local communication with multiple companion computing devices utilizes various other means of local communication (e.g. WiFi, short-wavelength radio wave communication such as Bluetooth, or any form of peer-to-peer communications). The system can further include a first portable non-wearable computing device of the user, typically a personal smartphone or tablet, that adapted to pair with the wearable device so as to allow subsequent exchanges of a first set of health data to the first computing device. The health data includes the health parameters detected by the one or more sensors. The system further includes a second non-wearable computing device of a third party that is adapted to pair with the wearable device so as to allow subsequent exchanges of a second plurality health data to the second computing device. The second set of health data including at least some of the one or more health parameters detected by the one or more sensors. In some embodiments, the second set of health data includes only health research related data.

In one aspect, the first computing device is a smartphone or tablet associated with the user and the second computing device is a smartphone and/or tablet associated with a local third party physician and/or researcher. In some embodiments, the wearable device is configured such that the user interface presents the detected health parameters to the user by providing an audio, visual or tactile indicator. In certain aspects, the wearable device is paired with the research computing device to facilitate location communication, such as by near field communication or by a physical connection. In some embodiments, the wearable sensor device is configured such that the first and second computing can be locally paired with the wearable device concurrently.

In another aspect, the first and second pairing of the wearable sensor device with the first and second computing devices are different from each other. The first and second pairing may utilize different user IDs. In some embodiments, the first pairing utilizes the same user ID as the first portable computing device. The second pairing utilizes a second pairing ID that is associated with a local third party researcher. In some embodiments, the second pairing operation can be performed on multiple devices associated with the second pairing ID. In one aspect, the first pairing user ID, or at least the identity of the user associated with the user ID, is not determinable from the second pairing ID on the second computing devices.

In yet another aspect, pairing between the wearable sensor device and the first or second computing device is facilitated by one of physical contact and near field communication between the respective devices in a local setting. Physical contact can refer to "bumping" two devices together to initiate communication by near field communication or a direct connection by a data cable. In some embodiments, the wearable sensor device utilizes a field detect feature and the pairing computing device can enable a reader mode or feature of the device to allow communication and initiation of pairing. In some embodiments, the first pairing utilizes a first authentication authorizing communication of a first set of data and the second pairing utilizes a second authentication authorizing communication of a subset of the first set of data. Authorizing communication further can include a researcher requesting for the subset of the first set of data from the second computing device and a user opt-in approval for access to the subset of the first data set from the first computing device. Each of the pairings allow subsequent communications between paired devices to be pre-authenticated. In some embodiments, the second pairing is configured to require user opt-in and/or user confirmation received on the wearable device before completing pairing between the wearable device and the second computing device.

In yet another aspect, methods for facilitating research utilizing a wearable sensor device are provided herein. One such example method include steps of: sharing information between a wearable device and a first portable non-wearable computing device in a first pairing operation; wirelessly linking the wearable device and the first portable non-wearable computing device using at least some of the shared information; sharing information between the wearable device and a second non-wearable computing device in a second pairing operation; and wirelessly linking the wearable device and the second non-wearable computing device using at least some of the information shared in the second pairing operation.

In another aspect, an example method for facilitating research using a wearable sensor device includes steps of: sharing information between each of a plurality of wearable devices worn by a plurality of users and a first non-wearable computing device of a researcher in a pairing operation and wirelessly linking each wearable device and the first non-wearable computing device using at least some of the shared information from the respective wearable device. Once paired, the wearable sensor devices are used to sense one or more health parameters of each of the plurality of users. The method the includes locally communicating a first set of health data from each of the plurality of wearable devices to the first computing device with the wireless link, wherein the first set of health data includes at least some of the one or more health parameters. The first set of data includes only research related health data and the one or more health parameters also includes non-research related health data.

In another aspect, a wearable device having enhanced features that facilitate use of the wearable device for research purposes is provided herein. Such a wearable device can include an associated user ID is comprising, one or more sensors adapted for detecting one or more user health parameters while the device is being worn by a user; a wireless communication link adapted for near/local communication with multiple non-wearable computing devices including communications for pairing with each of the multiple computing devices and communications for transmitting one or more health parameters including at least one of research data and non-research data. The wearable device can further include a user interface for receiving user input and for outputting health information indications, and a control unit for controlling operation of the device between alternate modes, the alternate modes including: a standard mode in which the device communicates research data and non-research data, and a research mode in which the device communicates only research data.

In yet another aspect, methods for facilitating research utilizing such systems and wearable sensor devices are provided herein. Such methods include use of a wearable sensor device having multiple modes of operation, such as a standard operating mode and a research mode. In one such method, the method includes: switching the wearable device from a standard to a research mode, wherein in the standard mode the wearable device is paired with a personal computing device associated with a user ID of the user and locally communicates a plurality of health information to the personal computing device associated with the user ID; while in the research mode, locally pairing with at least one other computing device associated with a third party ID of a researcher; and while in the research mode, locally communicating at least some of the plurality of health data to the at least one other computing device associated with the third party ID. In some embodiments, switching between the standard mode and the research mode is effected in response to a user input received on a user interface of the wearable device.

In some embodiments, in the research mode, suspending one or more non-research related applications operating on the device to conserve resources for one or more research related applications operating on the device. In another aspect, when in the research mode, outputting an identification and/or subject locating output in response to a locating request from the at least one other computing device associated with the third party ID.

In some embodiments, the system includes an identification and/or subject locating output comprises outputting any of an ID, a subject name, a location, an image, and an audible sound to one or both of the wearable device and the at least one other computing device associated with the third party ID. Such a feature may be limited to use when in a research mode and be disabled when the wearable device is in a standard operating mode.

DETAILED DESCRIPTION OF THE INVENTION

Figure 1:
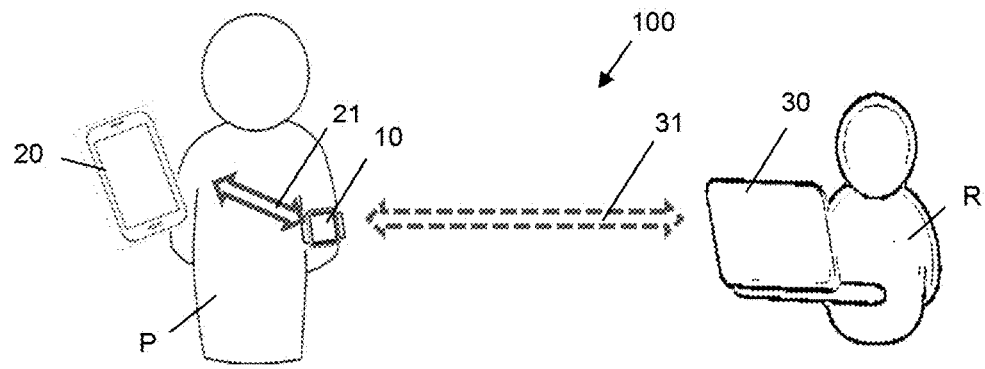
FIG. 1 is a simplified schematic illustrating a system for facilitating research having a wearable sensor device paired with both a personal computing device of the user and a computing device of a researcher in accordance with some embodiments of the invention.

In the following description, various examples will be described. For purposes of explanation, specific configurations and details are set forth in order to provide a thorough understanding of the examples. However, it will also be apparent to one skilled in the art that the examples may be practiced without the specific details. Furthermore, well-known features may be omitted or simplified so as not to obscure the example being described.

Embodiments of the invention pertain to wearable sensor device that allow for pairing with one or more research computing device in addition to pairing with a personal computing device of the user. This allows at least some health data obtained by such a wearable computing device to be directly monitored and tracked by researchers in a health research study, whereas, otherwise such information would be available only indirectly through a personal computing device of the user paired with the wearable sensor device.

In one aspect, the computing device is configured to receive health information of a user wearing the device. Such health information includes health parameters detected by one or more sensors associated with the wearable device, which may include a sensor integrated within the wearable device and one or more external sensors in communication with the wearable device. Such health information may also include various other types of health information received by the device, which may include: health information from the participants electronic medical record (EMR) accessed through a server communicatively coupled with the first portable device, or health information on a database, which may include health information entered by the user or obtained by the user (e.g., personal information collected by one or more wearable sensor devices and/or stored in a portable electronic device of the user). In some embodiments, this can include accessing the individual's health information through the personal wearing computing device of the individual, which can include accessing the individuals EMR and decrypting personal health information and communicating the health information to the researcher's computing device encrypted. By allowing a second pairing with one or more research devices, a large volume of health information can be readily received in real-time from multiple research participants, thereby facilitating research without requiring dedicated wearable sensor devices.

In another aspect, the wearable computing device includes a control unit that provides for a second pairing operation that is different from a first pairing, typically used with a personal computing device of the user. The second pairing may include one or more additional features that facilitate research, such as: allowing communication of a subset of health data that relates to the research study, prompting the user for authorization or an opt-in before communicating data, and modifying operation of the wearable device based one or more needs relating to operation of research related application or obtaining health information for research purposes. In addition, the second pairing may utilize an anonymous user ID from which the identity of the research participant cannot be determined. In addition, the second pairing may utilize a common user ID that is associate with one or more researchers, thereby enabling pairing with a second device or multiple other research devices.

In some embodiments, the system is configured to segregate health information of the user such that the researchers may only access health information that the user has authorized release of or has intentionally included in information to be released for research. In certain other aspects, the health information may undergo de-identification such that the health information may be used for research without being associated with any particular user. This aspect facilitates research with a wearable sensor device containing personal health data while maintained security and privacy of the personal health data of the user.

In one aspect, the system may be implemented as a computing device configured with a memory and a processor. The processor may be configured to execute instructions stored on the memory to run the first-party application framework and to receive one or more modules from a third-party researcher in order to present research study information to a user, recruit the participant for the research study, obtain informed consent from the participant, as well as conduct surveys and obtain information regarding various tasks pertinent to the research study. The first-party application framework may also utilize one or more modules developed by the first-party in accordance with certain requirements selected by the third-party researcher.

Embodiments of the present disclosure are directed to, among other things, managing personal information received from external sources, or from other peripheral devices of a user or a third-party researcher. In some examples, the information collected by the data collection devices may be provided to a wearable sensor device of the user (e.g., a smartwatch, arm band) and/or one or more first-party or third-party applications of the user device, before being selectively transmitted to a researcher for a treatment. In some examples, a first-party application may be one that is provided with the operating system (O/S) of the user device, is configured to operate natively with the user device, provided by the developers of the O/S for use with the user device, and/or trusted by the O/S and/or device.

In some aspects, a third-party research application may be one that is provided by a third-party researcher or entity other than the developer/manufacturer of the user device and/or it's O/S. Examples of information being collected and/or managed may be health, fitness, and/or activity information of the user (e.g., blood glucose levels, weight, height, calories burned, heart rate, etc.). The user information may be categorized or otherwise identified by one or more data types (or categories). Weight, number of steps walked, number of calories burned, heart rate, etc., are each an example of such health data. Other data types (e.g., outside of health information) are also envisioned including, but not limited to, hours worked, hourly rate, miles per hour, pages read per minute, etc. A computing device of the researcher allows for pairing and/or a request of health information relevant to research, while the user device of the user can determine a subset of the available health information that complies with requested data set as well as any authorization set by the user.

I. System Overview

FIG. 1 illustrates a simplified diagram of a system 100 that facilitates health research by pairing a wearable sensor device 10 (e.g. smartwatch) with a research computing device 30 associated with one or more researchers R. In particular, the system 100 allows use of a personal wearable computing device 10 for research purposes, the device 10 being configured to pair with a personal computing device 20 of the user (e.g. smartphone, tablet) in a first pairing operation 21. Typically, the wearable device 10 is worn by the user during pairing and personal computing device is associated with the user, although in some cases the personal computing device 20 may be associated with a parent or caretaker of the user. It is appreciated that while the user is usually human, the wearer of the device could include animals, both wild and domesticated fitted with wearable devices for the purpose of research and data collection.

In one aspect, the wearable device 10 is configured to "pair" with an external computing device in order to facilitate communication of health data obtained with the wearable data. "Pairing" typically refers to a sharing of data between the wearable device 10 and the external computing device utilizing a passkey associated with the wearable device 10 to facilitate subsequent communications between paired devices. Typically, the passkey is encrypted and stored on the external computing device or stored so as to be readily accessible by the external computing device, so that in subsequent communications, the passkey is accessed so that each subsequent communication does not require authentication and/or authorization. Once the pairing operation is performed, the devices remain paired so that subsequent communications are pre-authorized and communications from the wearable device can be readily associated with the wearable device without requiring repeating of the entire authentication procedure. It is appreciated that "pairing" may utilize various differing standards and/or encryptions (e.g. encryption handshake), all of which are encompassed by the "pairing operation" referred to throughout the present application.

In some embodiments, health information may be input directly into the wearable device 10 by the user through a user interface or may be obtained through one or more health information acquisition devices or sensors, that measure one or more health parameters that can be used to determine health data, either directly or indirectly. For example, the wearable device 10 may measure body temperature directly by one or more integrated sensor or may measure activity levels by wirelessly receiving measurement from of one or more accelerators.

In some embodiments, one or more sensor devices may be specialized for sensing and/or measuring various health metrics, including but not limited to activity level, activity tracking, respiration, body temperature, heart research related health data, hydration levels, perspiration, blood glucose, salinity, sleep cycles, posture, $O_2$ levels, muscle engagement, or any combination thereof. The collected data may or may not be specific to the condition being analyzed in the study and may be collected without requiring any additional input from the user to initiate collection of the sensed data. In some embodiments, the sensed data is collected over a duration of time, the duration generally exceeding a few days, such one or more weeks, months or years. Typically, these auxiliary health sensor devices are third-party devices that are supported by a third-party application and managed by used of a third-party service provider. Such sensors may also be a regulated medical device that is supported through a regulated medical service provider.

In one aspect, providing a wearable sensor device 10 that pairs with both a research device in addition pairing with a personal computing device allows for at least several different system configurations that are advantageous for use in research studies. Examples of such configurations are shown in FIGS. 1 and 2A-2B.

As shown in FIG. 1, system 100 utilizes a wearable portable computing device 10 (e.g. smartwatch device), which is suited for use as a personal device of the user wearing the device, for research purposes. Typically, such a wearable device 100 is paired and communicatively linked by a first pairing operation 21 with a personal portable computing device 20 (e.g. a smartphone, tablet or other non-wearable computing device) that is associated with the user P such that pairing and communication is limited to the personal device of the user P or associated caretaker. Such a configuration has been considered desirable since this helps secures a user's private health information. In the present system, wearable device 10 is configured to pair with a second computing device 30 associated with a researcher R in a second pairing operation in addition to the first pairing with a first computing device of the user. Such a configuration allows the various features of the wearable device that were previously available only to the user to be made available for research purposes as well.

Figure 2A:
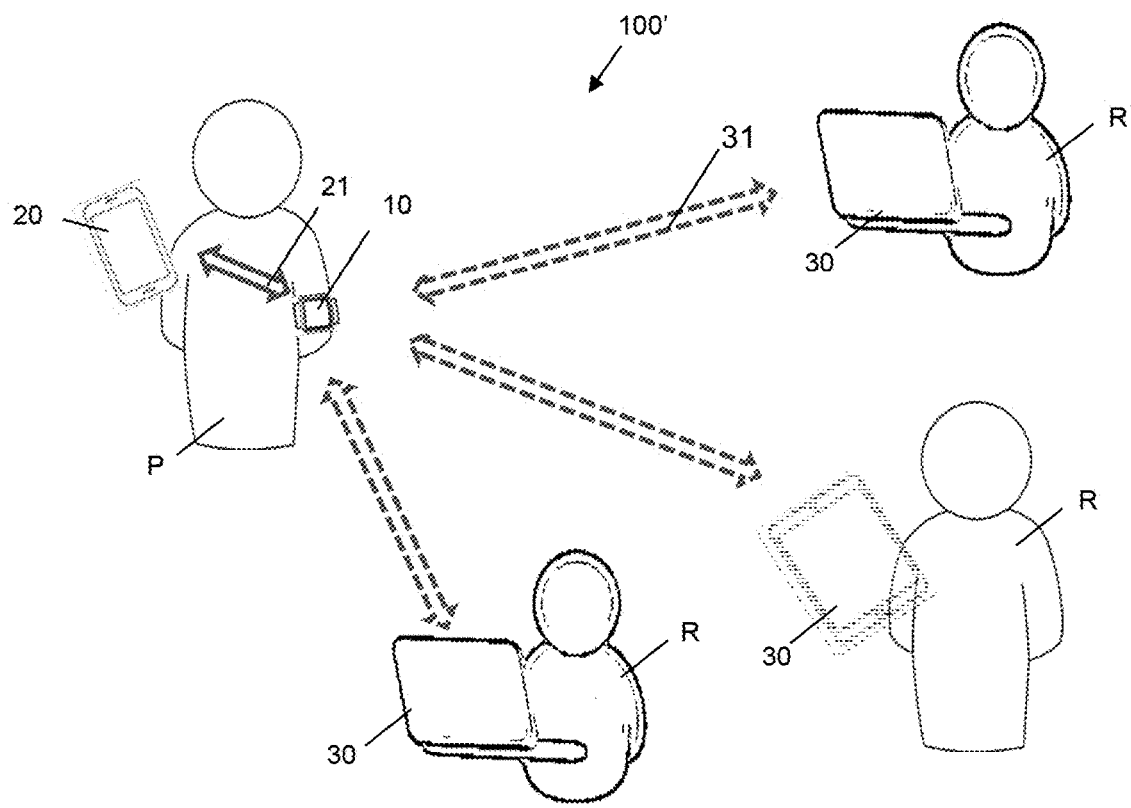
FIG. 2A is a simplified schematic illustrating a system for facilitating research having a wearable sensor device paired with multiple computing devices of researchers in accordance with some embodiments.
Figure 2B:
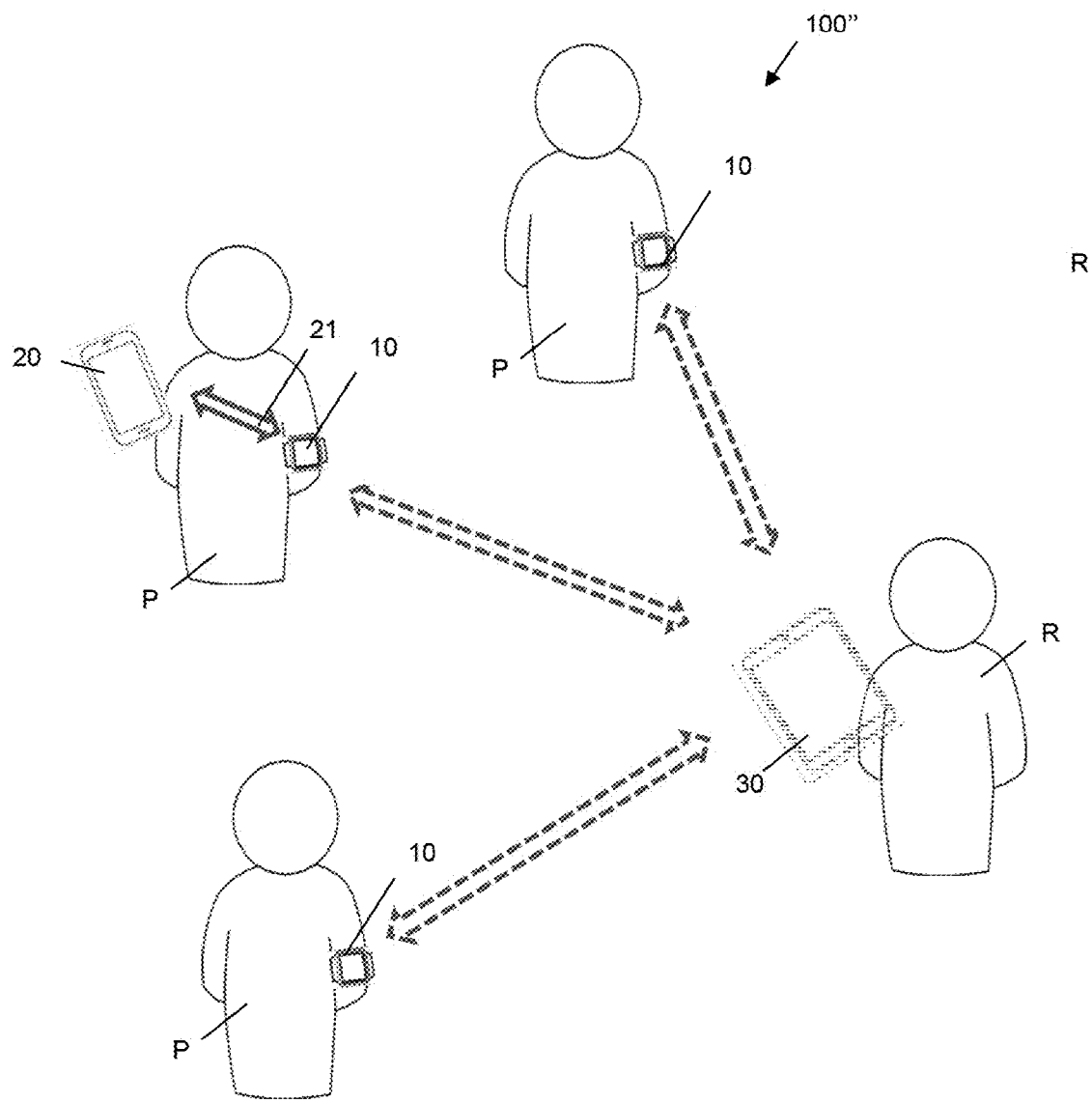
FIG. 2B is a simplified schematic illustrating a system for facilitating research having multiple wearable sensor devices paired with a common research computing device in accordance with some embodiments.

FIG. 2A illustrates another system 100' that facilitates health research that utilizes a wearable sensor device 10 suited for pairing and communicatively linking with a personal portable computing device 10. In this system, the second pairing operation is utilize to pair the wearable sensor device to multiple non-wearable computing devices 30 associated with one or more researchers R. In some embodiments, the second pairing operations utilize a common identifier and/or researcher user ID such that the linking is substantially identical as is the information being communication through the second pairing link. This facilitates sharing of common information between the multiple research computing devices 30 by direct local communication with the wearable sensor device 10. In other embodiments, the second pairing operation may be performed with multiple research devices and utilize differing pairing IDs. This may facilitate communication of differing types of health data to differing researchers, for example, a first researcher may request temperature data and blood oxygen levels through one pairing link with one research computing device and a second researcher may request heart rate data through another paired link with another research computing device 30. Optionally, in some embodiments, the research subject can select a type of data exchange and the type of data that is shared with the researchers, as well as which researcher a particular set of data is shared with. These differing research IDs may be associated with each other through a common identifier to facilitate concurrent information exchange between the multiple research computing devices 30 and the wearable sensor device 10. In some embodiments, the research user ID is a user ID of the research device, which is associated with the researcher. In other embodiments, the multiple devices utilize a common research user ID such that each can be linked to the wearable device by a pairing operation.

As described above, the pairing operation involves an exchange of information (e.g. encryption handshake), at least some of which is stored on the device (e.g. encrypted passkey) so as to establish a link that pre-authenticate subsequent communications by accessing the passkey. Typically, specific information (e.g. a passkey) is stored on the computing device paired with the wearable device during the pairing operation. In one aspect, the second pairing operation is different from the first pairing operation, for example, the specific information used in the second pairing is different from the specific information used in the first pairing. This configuration allows the distinctions to be readily recognized and observed in the types of health information communication with the first and second pairing links. In some embodiments, the first pairing utilizes a user ID of the first portable computing device (e.g. smartphone, tablet), which is typically a user ID associated with the user P, while the second pairing utilizes a research user ID associated with one or more researchers.

In some embodiments, each of the multiple research devices is paired separately with the wearable device by a separate pairing operation. The pairing operations may utilize a common identifier and/or research user ID such that the communication link is substantially identical and facilitates local communication of like health data to each of the paired research devices from the wearable sensor device 10. Alternatively, in some embodiments having multiple research devices, the multiple research devices utilize a common research user ID and are in communication with each other such that specific information can be accessed by each of the research devices. This can be used to establish pairing between each of the multiple research devices and the wearable sensor device 10 upon pairing of the device 10 with any the research devices is performed.

FIG. 2B illustrates another system 100' that facilitates health research by utilizing a wearable sensor device 10 suited for pairing and communicatively linking with a personal portable computing device 10. In this system, the second pairing operation is utilize to each of the plurality of wearable sensor devices with a common research computing device 30. In some embodiments, when pairing multiple wearable sensor device with one or more research devices, the system enable communication of additional meta data about each wearable device to the research device. This allows the research computing device to differential between the multiple wearable sensor devices. Such data can include: location, name or subject ID, photo of the subject, a password, or other information specific to a particular subject. While this aspect is particularly useful in organizing and managing health data received from multiple wearable devices, it is appreciated that this aspect is not required. For example, in some research studies where overall trends may be of interest, the ability to distinguish health information from individual wearable sensor devices may not be needed.

Figure 3:
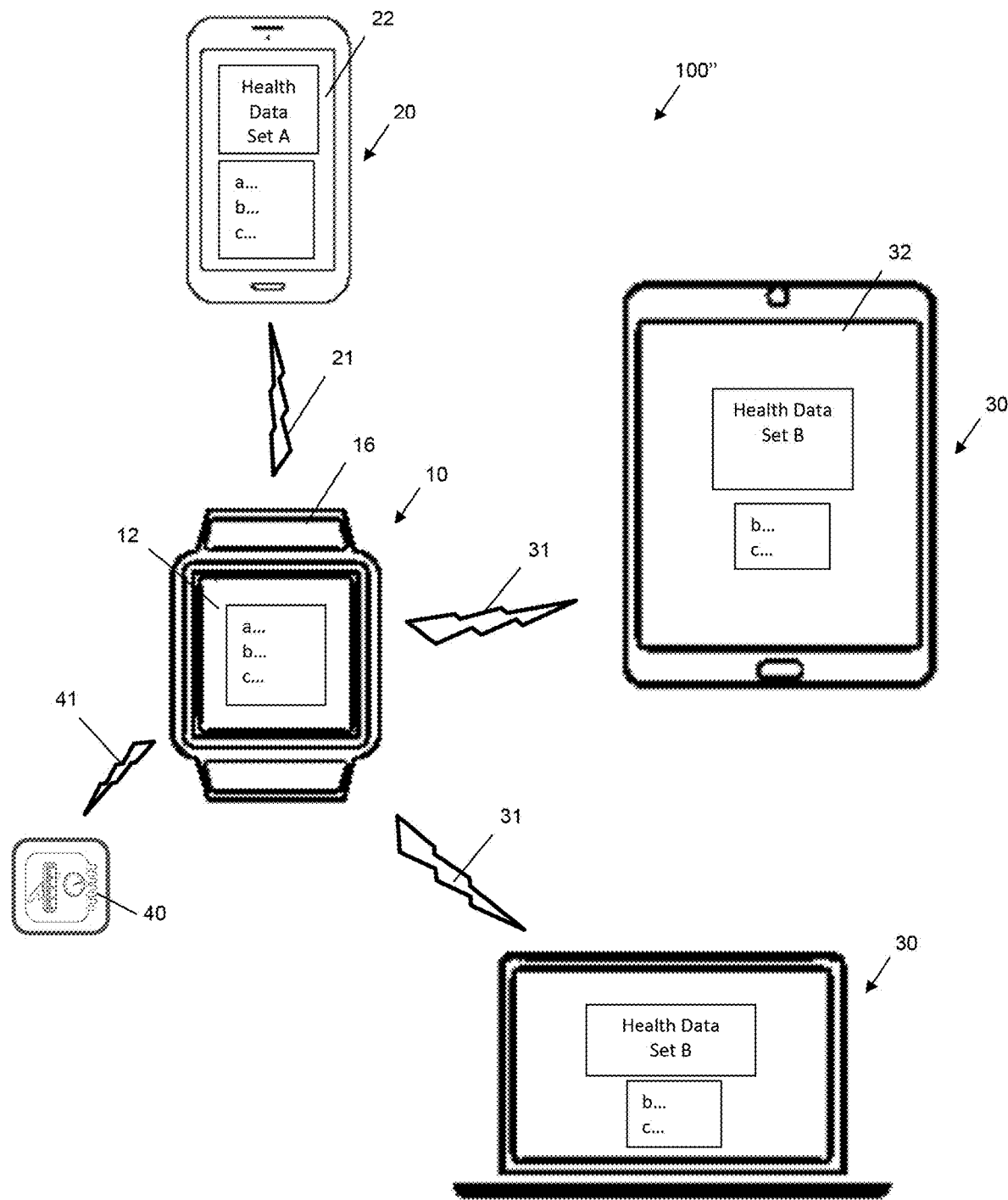
FIG. 3 is a schematic illustrating communication of health information in a system for facilitating research with a wearable device in accordance with some embodiments.

FIG. 3 illustrates a system 100''' that facilitates health research by utilizing a wearable device 10 (e.g. smartwatch) in accordance with aspects of the invention. Wearable device 10 includes one or more integrated sensors (not shown) that detect health parameters of the user when the device is worn by a user. In this embodiment, the wearable device 10 is a smartwatch having a strap 16 such that the device is worn on a wrist of a user and a user interface 12 is provided on a face of the smartwatch. The system further includes a specialized auxiliary sensor device 40 (e.g. heart monitor patch, ECG, blood glucose sensor, etc.) having a wireless communication link 41 (e.g. Bluetooth) with the smartwatch device. The auxiliary sensor device 40 may be used when detection of a health parameter that is not otherwise obtained by sensors integrated within the wearable device 20 is desired by the user and/or the researcher. Health parameters sensed by the auxiliary sensor device 40 are received by the wearable device 10 and stored along with one or more health parameters sensed by any sensors integrated within the wearable device. Health data can then be wireless transmitted, such as by local communication (e.g. NFC), to a personal computing device 20 of the user by a first pairing communication link 21 and to research computing device 30 by second pairing communication links 31. Typically, the personal computing device 20 includes a user interface 22 on which the user can view health information received from the wearable sensor device. Likewise, the research computing devices 30 also include user interface 32 on which a research can view and/or manage health data received from the wearable sensor device.

II. Segregation of Health Data

In one aspect, the wearable device includes a control unit that communicates health data to each of the computing devices with which the wearable device is paired. In some embodiments, the control unit is configured to locally communicate a first set of the health data accessed by the wearable device via a wireless link established by the first pairing and configured to locally communication a second set of the health data via a wireless link established by the second pairing. In one aspect, the health data stored and/or accessed by the wearable device includes both research related health data and non-research related health data. In some embodiments, the first set of health data includes any of the health data stored and/or accessed by the wearable device and the second set of health data is a subset of the first set of health data that includes only research related health data.

In some embodiments, the second set of health data may include only health data from the first set that has been authorized by the user for communication to third-parties. In some embodiments, the second set of data may include one or more health parameters that are not included in the first set. For example, a researcher may provide a specialized auxiliary sensor 40 that provides a health parameter that is provided to the researcher via the link of the second pairing that is not communicated to the first portable computing device of the user. This may be performed by use of a health related application to communicate the health parameter to the second computing device associated with the researcher or by encryption of the parameter such that decryption is provided only by the second computing device of the researcher.

As can be seen in FIG. 3, the health data received by the first computing device 20 (Health Data Set A) can differ from the health data received by the research computing devices 30 (Health Data Set B). In this embodiment, Health Data Set B is a subset of Health Data Set A that relates to research. This distinction in types of health data that can be sent can be associated with the researched ID associated with the second pairing or may be facilitated by an exchange of information (e.g. request from researcher, opt-out by patient) that is initiated through the second pairing communication link. This distinction may also be facilitated by one or more health research related application associated with the researcher than determine what types/kinds of health data are research related and requests only that subset of data from all available health data.

The health information obtained by the wearable sensor device from one or more sensors may be specialized for sensing and/or measuring various health metrics, including but not limited to activity level, activity tracking, respiration, body temperature, heart research related health data, hydration levels, perspiration, blood glucose, salinity, sleep cycles, posture, $O_2$ levels, muscle engagement, or any combination thereof. The collected data may or may not be specific to the condition being analyzed in the study and may be collected without requiring any additional input from the user to initiate collection of the sensed data. In some embodiments, the sensed data is collected over a duration of time, the duration generally exceeding a few days, such one or more weeks, months or years. Typically, these auxiliary health sensor devices 103 are third-party devices that are supported by a third-party application and managed by a third-party service provider. Such sensors may also be a regulated medical device that is supported through a regulated medical service provider 301. The wearable sensor device 102 communicates the health information to the user data server 320, which may be selectively accessed by the researcher data system based on identification of a subset of data authorized by the user to be released by the researcher.

Figure 4:
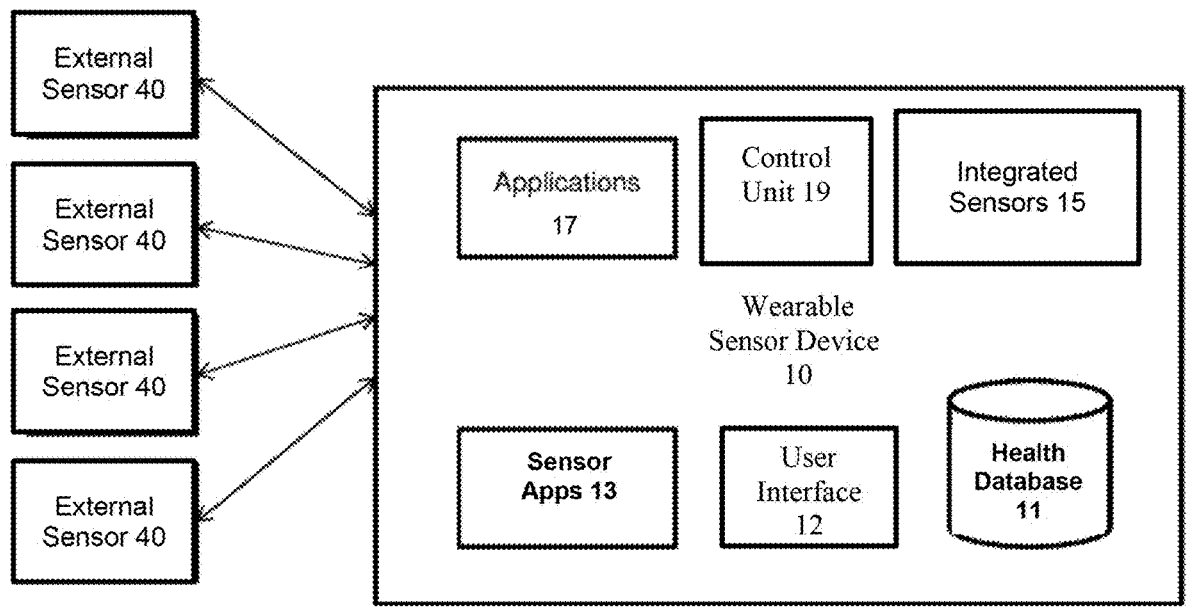
FIG. 4 is a schematic of an example wearable user device for use in a system for facilitating research in accordance with some embodiments.

FIG. 4 illustrates an example wearable sensing device 10 for receiving health information from a user. Such health information can include, but is not limited to, any type of data associated with a person's health, such as weight, heart rate, blood pressure, blood glucose level, medication compliance, activity level, or the like. Wearable sensing device 10 can be used to collect research related health data associated with a user, store the research related health data and present the research related health data to the user in useful ways, such as on a user interface 12 of the wearable device 10. Wearable sensor device 10 can further be used to collect non-research related health data along with research related health data, correlate the non-research related health data with the research related health data, and display the non-research related health data with the research related health data.

In one aspect, wearable sensor device 10 can include can include an operating system and a wellness or health information database 11 for securely storing wellness or non-research related health data along with associated metadata, such as the time the data was recorded, type of data, device used to record the data, user associated with the data, and the like. Wearable sensor device 110 can further include application programming interfaces (APIs) with access controls for storing data in the health information database 11 and for accessing data stored in the health database 11. Wearable sensor device 110 can be configured to receive wellness or non-research related health data from various sources and can store the received data in the research related health database. For example, wearable device 10 can be configured to receive wellness or non-research related health data from integrated sensors 15 of the wearable sensor device or from external sensors 40.

Such sensors can include any type of sensor capable of obtaining research related health data, such as a biometric sensor, activity tracker, or the like. For example, sensors 40 can include, but are not limited to, a scale, blood pressure cuff, blood glucose monitor, electrocardiogram, step counter, gyroscope, accelerometer, SpO2 sensor, respiration sensor, posture sensor, stress sensor, photoplethysmogram, galvanic skin response sensor, temperature sensor, asthma inhaler, or the like. Sensors 40 can also include other types of sensors, such as audio sensors, ambient light sensors, electromagnetic sensors, touch sensors, capacitive sensors, and the like, for obtaining non-research related health data, such as situational data, temporal data, personal data, contact data, and the like data. While specific examples are provided, it should be appreciated that various other sensors can be used and other combinations of sensors can be combined into a single device. These sensors can be used to measure wellness or non-research related health data continuously, intermittently, periodically, or at any other desired frequency or interval of time. For example, external sensors 40 can be used to obtain a single measurement or multiple measurements over a length of time. Additionally, sensors 40 can be used to measure wellness or non-research related health data at any time or location desired by the user.

In another aspect, wearable sensor device 10 can include software sensor applications 13 (e.g., third party applications) associated with each of external sensors 40 for interfacing with the sensors to allow wearable sensor device 10 to receive the health or non-health related data. In these examples, the applications 13 can use the device's APIs to store the wellness or non-research related health data in the health information database 11 of device 110. In some examples, the software sensor applications 13 can be Apps and wearable device 10 can be a smartwatch worn on a wrist of the user. It should be understood that "third party" can correspond to an entity different than the manufacturer of device 10 and/or the entity that created and/or maintains the operating system of device 110. In these instances, third party applications and their corresponding sensors can communicate and function within the operating system of device 10 according to a predefined device protocol associated with device 10. Applications 13 can similarly use the device's APIs to access data stored in the research related health database 11. In other examples, wearable sensor device 10 can be configured to share one or more communication formats with sensors 40 to allow sensor device 10 to receive and interpret the wellness or non-research related health data from the sensors. The received data can then be stored in the research related health database 11 of wearable device 10.

In some examples, default or user-selected settings can be provided to restrict the access that at least one application (e.g., at least one of applications 13 and 17) on wearable device 10 has to the health database 11 of wearable device 10 (for both storage and retrieval purposes) and to the sensor data generated by sensors 15 within wearable device 10 and/or sensor data generated by sensors 40. For example, an application for tracking a user's running sessions can be granted access to the data generated by the GPS sensor of wearable device 10, but can be prevented from accessing the user's blood pressure data stored in the health database 11. In some examples, an entity other than the owner of wearable device 10 can set the authorization settings for various applications on wearable device 10. For example, the manufacturer of wearable device 10 and/or the entity that created and/or maintains the operating system of wearable device 10 can evaluate the applications to determine if they should be given access to the user's research related health data and/or sensor data generated or received by wearable device 10. In some examples, these settings can be overridden by the user.

In some embodiments, the wearable sensor device 10 may include at least one memory and one or more processing units or processors. The processors may be implemented as appropriate in hardware, software (e.g., computer-executable instructions, firmware, etc.), or combinations thereof. Computer-executable instruction or firmware implementations of the processors may include machine-executable instructions written in any suitable programming language to perform the various functions described. The memory may store program instructions that are loadable and executable on the processors, as well as data generated during the execution of these programs. Depending on the configuration and type of wearable sensor device 10, the memory may be volatile (e.g., random access memory (RAM)) and/or non-volatile (e.g., read-only memory (ROM), flash memory, etc.). The wearable device 10 may also include additional removable storage and/or non-removable storage including, but not limited to, magnetic storage, optical disks, etc. The disk drives and their associated non-transitory computer-readable media may provide non-volatile storage of computer-readable instructions, program modules, data structures, and other data for the computing devices. In some implementations, the memory may include multiple different types of memory, such as RAM, static random access memory (SRAM), dynamic random access memory (DRAM), or ROM. While the volatile memory described herein may be referred to as RAM, any volatile memory would be appropriate.

In another aspect, the memory and processor of the wearable device may be incorporated into a control unit 19 configured to perform data acquisition from one or more sensors associated with the device, determination of research related health data and/or non-research related health data, pairing with one or more computing devices and communication of specific health data to one or more computing devices paired with the wearable device. Control unit 19 may include with one or more modules pre-configured to perform one or more specific tasks or procedures. For example, such modules may include a communication module that performs a communication operation of specific health data based on one or more variable, such as a type of pairing and/or a user input received by the device. Another type of module may include a data acquisition module that obtains health parameters from one or more sensors associated with the wearable device 10 and manages and stores the health parameters within a health information database on the device 10.

Additional types of computer storage media that may be present in the wearable device 10 may include, but are not limited to, phase-change RAM (PRAM), SRAM, electrically erasable programmable read-only memory (EEPROM), flash memory, compact disc read-only memory (CD-ROM), digital video disc (DVD), magnetic cassettes or tape, magnetic disk storage, or any other medium that can be used to store the desired information and that can be accessed by the wearable sensor device 102. Combinations of any of the above should also be included within the scope of non-transitory computer-readable media. Alternatively, computer-readable communication media may include computer-readable instructions, program modules, or other data transmitted within a data signal, such as a carrier wave, or other transmission. However, as used herein, computer-readable storage media does not include computer-readable communication media. The wearable device 10 may also contain communications connections that allow the wearable device 10 to communicate with a data store (e.g., the database 109), or another computing device via one or more networks. The wearable device 10 may also include I/O devices, such as a keyboard, a mouse, a pen, a voice input device, a touch input device, a display, speakers, etc.

Turning to the contents of the memory in more detail, the memory may include an operating system and/or one or more application programs or services for implementing any of the features disclosed herein. A background module may be configured to launch and/or relaunch third-party applications in as background process based on an operating mode of the wearable device. In some examples, the background module 336 may also be configured to verify that the third-party application has finished processing the data it requested, by continuing to relaunch the third-party application in the background until notification is received that the third-party application has completed processing. Further, the aggregation module may be configured to aggregate or otherwise combine (and, in some examples, provide presentation for) user data received from multiple different data sources.

In any of the embodiments described herein, any local communication between the wearable device and a non-wearable computing device of the user and a researcher can be performed by magnetic induction (e.g. near field communication) and/or radio based communication, such as short-wavelength radio communication (e.g. Bluetooth) or wireless local area network (e.g. WiFi, an ad hoc network, peer-to-peer). In some embodiments, near field communication is utilized in an initial pairing operation (e.g. transferring of keys, passcodes, and other associated information) for the purposes of simplifying/automated subsequent exchanges of information, while local communication after the initial pairing can utilize radio-based communication, such as Bluetooth or WiFi, to allow subsequent exchanges of data over greater distances but still in relatively close proximity without requiring use of a remote server or network. In some embodiments, this latter type of communication can be accomplished either through: ad-hoc peer-to-peer communications (e.g. short communications that are within view or within the propagational limitations of the radios or another room but still in close proximity); or while being "associated" with another device whereby local communications are potentially continuous, but still within close proximity. In some embodiments, when each device detects the ID of the other, pairing or association occurs and the devices remain connected as long as they remain in sufficient proximity.

III. Example Systems

A. Wearable Device Paired with Personal Device and Research Device

Currently, wearable sensor devices suited for personal use can typically only be paired with a single companion device. Since the health data is personal to the user and security and privacy of the health information is of the utmost importance, it had been considered desirable to restrict pairing of the wearable sensor device with external computing device such that communication of the health information was restricted and more secure. While such wearable devices have proven extremely useful for personal health tracking in allowing a user to monitor their own health parameters and selectively manage their own health data on their personal smartphone, their usefulness in research is hindered by these limitations. For example, while a researcher could utilize health information obtained by such a device, a researcher cannot readily access the health data without the user selectively outputting the health data through another device, which may be time-consuming and require a sequence of steps that many users may be unlikely to perform. In addition, receipt of such health data may not be in real-time such that a research study requiring interactivity between researchers and participants during a session based on accumulated health data may not be feasible. Even if transfer of health data could be effectively and quickly managed by means of various applications or software, this process may be cumbersome and would not fully utilize the enhanced performance and capabilities of the wearable device that are realized during personal health tracking performed by the user.

By configuring the wearable sensor device to be paired with a second computing device associated with a researcher, in addition to the pairing with a first computing device of the user, the features of the wearable sensor device can be fully realized within a health research context. Pairing with multiple devices does, however, raise the concern of undesirable dissemination of personal, private health information stored by the wearable sensor device. To alleviate security and privacy concerns in regard to multiple pairings, the wearable sensor device is configured to pair with the second computing device, the research device 30, in a second pairing that is different than the first pairing with the first computing device (e.g. personal device, smartphone, tablet) of the user. Each pairing establishes a communication link that facilitates local communication of data in subsequent exchanges of data without requiring repeated exchanges for authenticating data sources and communications each time. In one aspect, the first pairing allows for the pairing and communication of data suitable for personal use of the wearable sensor device by the user, while the second pairing allows for communication and exchange of data that is suited for a particular research. Often, the second pairing is more restrictive than the first.

In some aspects, the first pairing utilizes a user ID of the personal computing device that is associated with the user, while the second pairing utilizes a research ID that is associated with one or more researchers. In some embodiments, the first pairing allows communication of any health information stored or accessed by the wearable sensor device to allow a user full access to their own personal health data. In some embodiments, the first pairing uses a unique user ID of the personal device 20 such that the first pairing can only be made with a single companion device at one time. The second pairing allows communication of a subset of data, such as only research related health information, to facilitate local communication of health data to the researcher during a study.

In some embodiments, the second pairings utilizing a research user ID associated with a researcher or research study such that the second pairing is not limited to pairing of a particular device with a unique user ID. This aspect allows for pairing of a single wearable sensor device 10 with multiple research computing devices 30, which is advantageous in that it allows multiple researchers ready access to health information relevant to the study.

Figure 5:
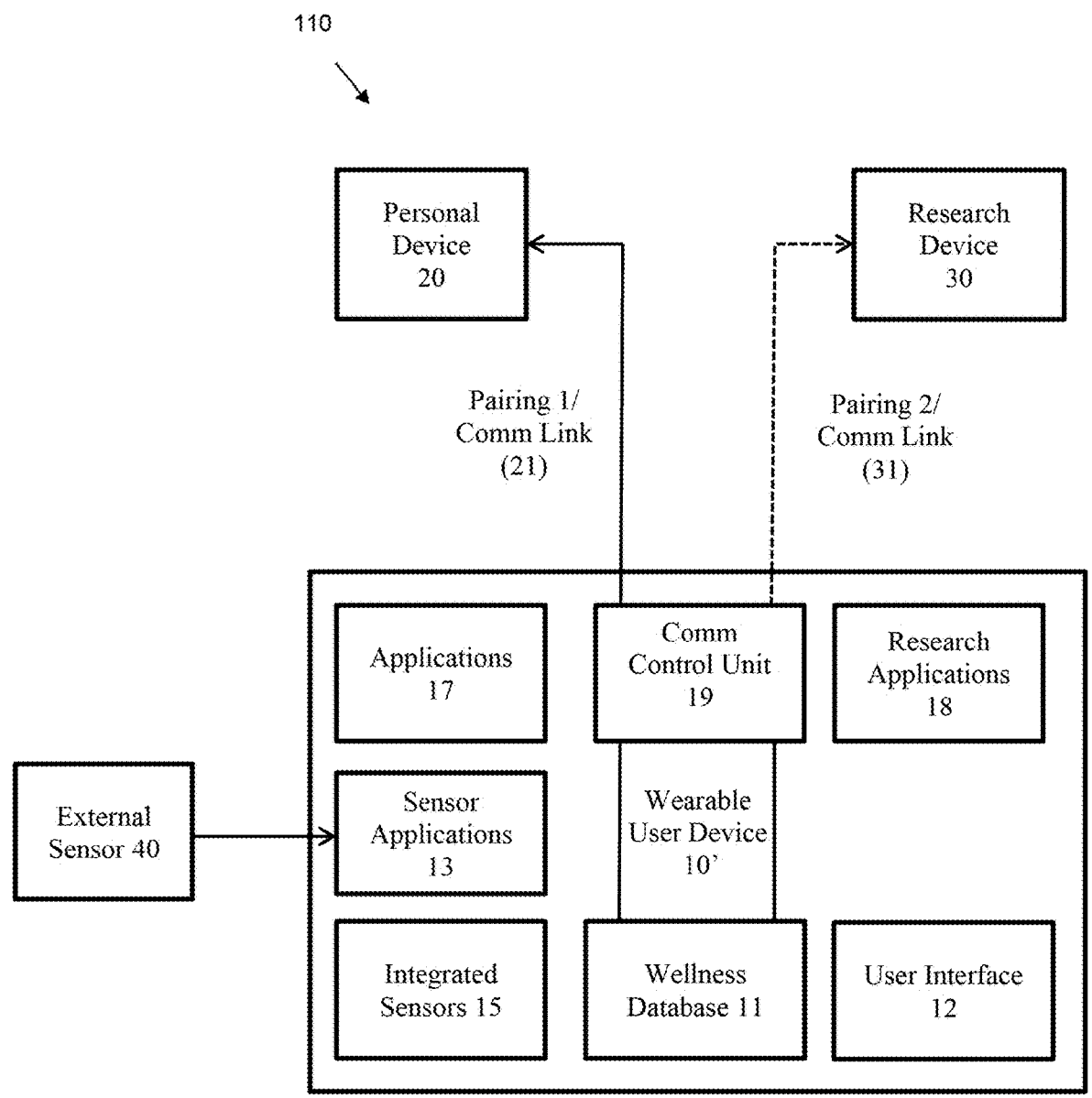
FIG. 5 is a schematic of an example system for facilitating research in accordance with some embodiments.

FIG. 5 illustrates a schematic depicting a system 110 for facilitating research by utilizing a wearable sensor device 10' that is paired with and in communication with each of a personal device 20 of the user and a research device 30 of a researcher. As described above, the wearable device 10 may include applications 17 and sensor applications 13 that facilitate detecting of health parameters from one or more integrated sensors 15 and/or one or more external sensors 40. The wearable device 10 may further include research specific applications 18, which may be first-party or third-party applications, that may be used in obtaining health information relating to a research study and/or determining whether health information obtained by the wearable device 10 is research related or non-research related. The research related applications may further be adapted to effect certain research related features, such as any of those described herein. A control unit 19 facilitates pairing with each of the personal computing device 20 and the research computing device 30 to establish a communication link between each as further facilitates subsequent communications of health information to each device. The control unit may include input from the applications 17, research applications 18 and/or a user input received via the user interface.

B. Wearable Device Paired with Multiple Research Devices

In another aspect, the system includes a wearable sensor device configured to performs a second pairing operation that utilizes a common ID, such as researcher user ID, such that the wearable sensor device can be paired with any computing device utilizing the researcher user ID. This approach allows the wearable device to be concurrently paired with multiple research devices with a same or differing communication link. Having like communication links for each of the multiple research computing devices is allows the same health information relevant to the research to be concurrently communicated to each of the multiple research devices. Such a configuration is particularly useful as it allows multiple researchers to easily manage, aggregate data, setup that would not otherwise be possible if the wearable device allowed only pairing to a single companion by the first pairing. This approach is further advantageous over using conventional pairing in that the second pairing allows for a communications link that is distinct from the first pairing, for example, the second pairing can be used to communication a limited subset of data and/or limited set of data that is authorized by a user via a user interface of the wearable sensor device. Such a configuration allows multiple researchers ready access to health information relevant to the research study while still safeguarding privacy and security of health data that is not research related.

Figure 6:
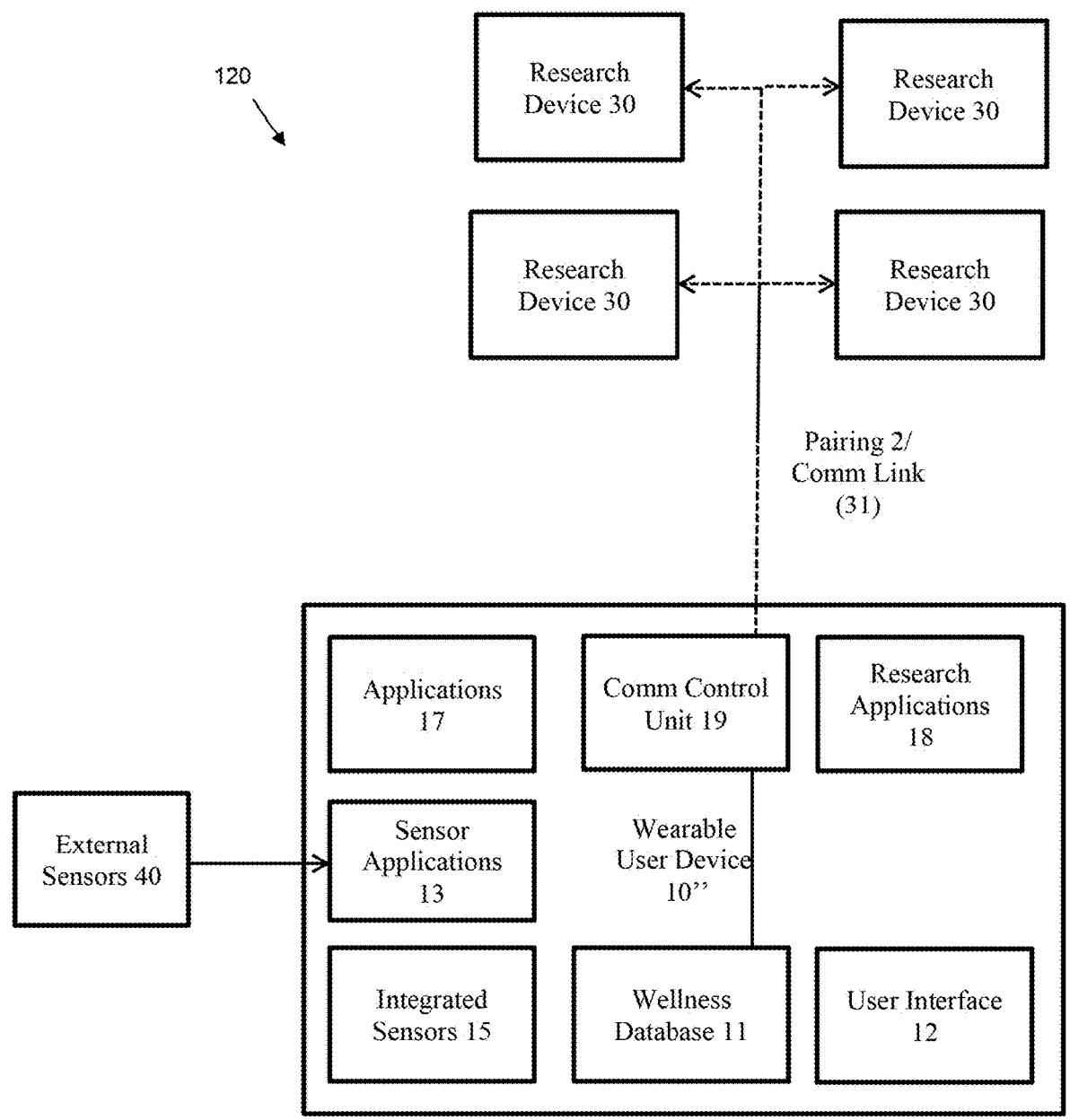
FIG. 6 is a schematic of an example system for facilitating research in accordance with some embodiments.

FIG. 6 illustrates a schematic depicting a system 120 for facilitating research by utilizing a wearable sensor device 10" that is paired with and in communication with each of a personal device 20 of the user and multiple research devices 30 associated with multiple researchers. In this example, the pairing is the same between all research devices such that the same health information can be locally communicated between the wearable sensor device and each research device. In this example, the wearable sensor device is not concurrently paired with a personal device associated with each user, although each wearable sensor device can be adapted for such a pairing. As described above, the wearable device 10 may include applications 17, sensor applications 13 that facilitate detecting of health parameters from one or more integrated sensors 15 or one or more external sensors 40. The wearable device 10 may further include research specific application 18 that may be used in obtaining health information relating to a research study and/or determining whether health information obtained by the wearable device 10 is research related or non-research related. The control unit 19 facilitates pairing with the personal computing device 20 and the research computing device 30 to establish a communication link between each as well as subsequent communications of health information to each, as described herein. The control unit may include input from the applications 17, research applications 18 and/or a user input received via the user interface.

While in many example embodiments, the wearable device is being shown as being concurrently paired with a personal computing device of the user and a research computing device of a researcher, it is appreciated that a first pairing to a personal computing device is not required for facilitating research using wearable computing device. For example, off-the shelf wearable sensor devices (e.g. smartwatches) can be distributed to a group of research participants without ever establishing a first pairing associated with a personal computing device of the user and can then be paired only with the one or more research computing devices 30. This allows researchers to utilize the advantageous features of off-the-shelf wearable sensor devices without interfacing with the user through personal computing devices.

In another aspect, it is appreciated that one or more of the multiple sensor devices may be paired with a respective personal computing device of a respective user in first pairing. This allows wearable sensor devices to be utilized for research purposes even when already set-up for personal use. This further reduces the costs and burden of developing and providing sensor equipment to research participants, costs which are often borne by the researchers. In some embodiments, once a wearable device is paired with a computing device of the researcher, data can be encrypted with the public key of the researcher and stored in the cloud. It can then subsequently be retrieved from the cloud and decrypted using the researcher's own private key. This approach is advantageous as it allows exchanged data to be fully encrypted and only accessible to those having the key.

In some embodiments, the wearable device is one of a plurality of wearable devices, each having been paired with a plurality of non-wearable computing devices associated with a plurality of researchers. In such embodiments, the wearable device can include a "find my subject" feature that allows a researcher to find a particular research subject from a plurality of subjects associated with the plurality of wearable devices. For example, a researcher using an associated non-wearable computing device can select which subject to locate, such as by pressing a button on a user interface, and create a tone/ping on the respective wearable device of the selected subject that identifies the subject. In some embodiments, the research computing devices can include a radio with time-of-flight capabilities. In such embodiments, where each wearable device is paired with a plurality of research computing device and each includes a radio antennae, multiple research devices can estimate a distance and/or direction of the research subject so as to allow localization of the subject.

C. Multiple Wearable Devices Paired with a Common Research Device

In another aspect, the system includes a wearable device configured to perform a second pairing that utilizes a common ID, such as a researcher ID, so as to allow multiple wearable sensor devices to be paired with a common research device. This allows a single researcher to track multiple research participants at one time. Such a configuration is particularly useful as it allows multiple researchers to easily manage, aggregate data from multiple wearable devices, setup and track multiple watch devices without obtaining multiple computing devices with unique user IDs, such as would be required if the wearable device allowed only pairing to a single companion by the first pairing. This feature allows a single research to directly compare like health parameters between multiple research participants, that may otherwise be too unwieldy to manage in real-time. Such a system may also include research applications that operate on the research computing devices so as to allow the researcher to quickly select, group, sort and otherwise manage health information between the different research participants from a single research computing devices.

In one aspect, although the second pairing operation that pairs each wearable device utilizes a common ID associated with the researcher and/or the researcher device, the pairing can also associate each wearable device with another participant ID for research purposes. Typically, the unique ID is distinct from the user ID associated with the user and any personal computing devices with which a respective wearable sensor device is paired in the first pairing operation. The participant ID may be any arbitrary ID, and for many types of research studies (e.g. blind, double-blind) are provided such that an identity of the user cannot be determined from the ID during the study. The determination of a unique participant IDs may be facilitated by research related applications operating on one or both of the research computing device and the wearable sensor device.

In another aspect, the wearable sensor devices may include an associating feature that allows a group of sensor devices to record and/or output an association to the research computing device. Such a feature may be advantageous for determining an initial grouping of participants in certain categories or groups (e.g. placebo, control group) without requiring knowledge of which participants are within which group by the researcher. In some embodiments, the association indicator is encrypted or inaccessible by the research computing device during the study so as to facilitate a double-blind research study. The associate may be established by detection of close proximity between wearable devices worn by user that are grouped together and/or by "bumping" or contacting exposed faces of wearable devices worn by adjacent users.

D. Multiple Modes of Operation

In yet another aspect, the system 130 includes a wearable sensor device 10''' having a control unit having multiple modes of operation that include a research mode adapted for providing any of the research features described herein. For example, in some embodiments, the association feature provided above may be provided only in the research mode and be disabled in a standard operating mode. Likewise, the capability to pair with one or more research computing devices in a second pairing operation may be provided only when operating in the research mode.

Figure 7:
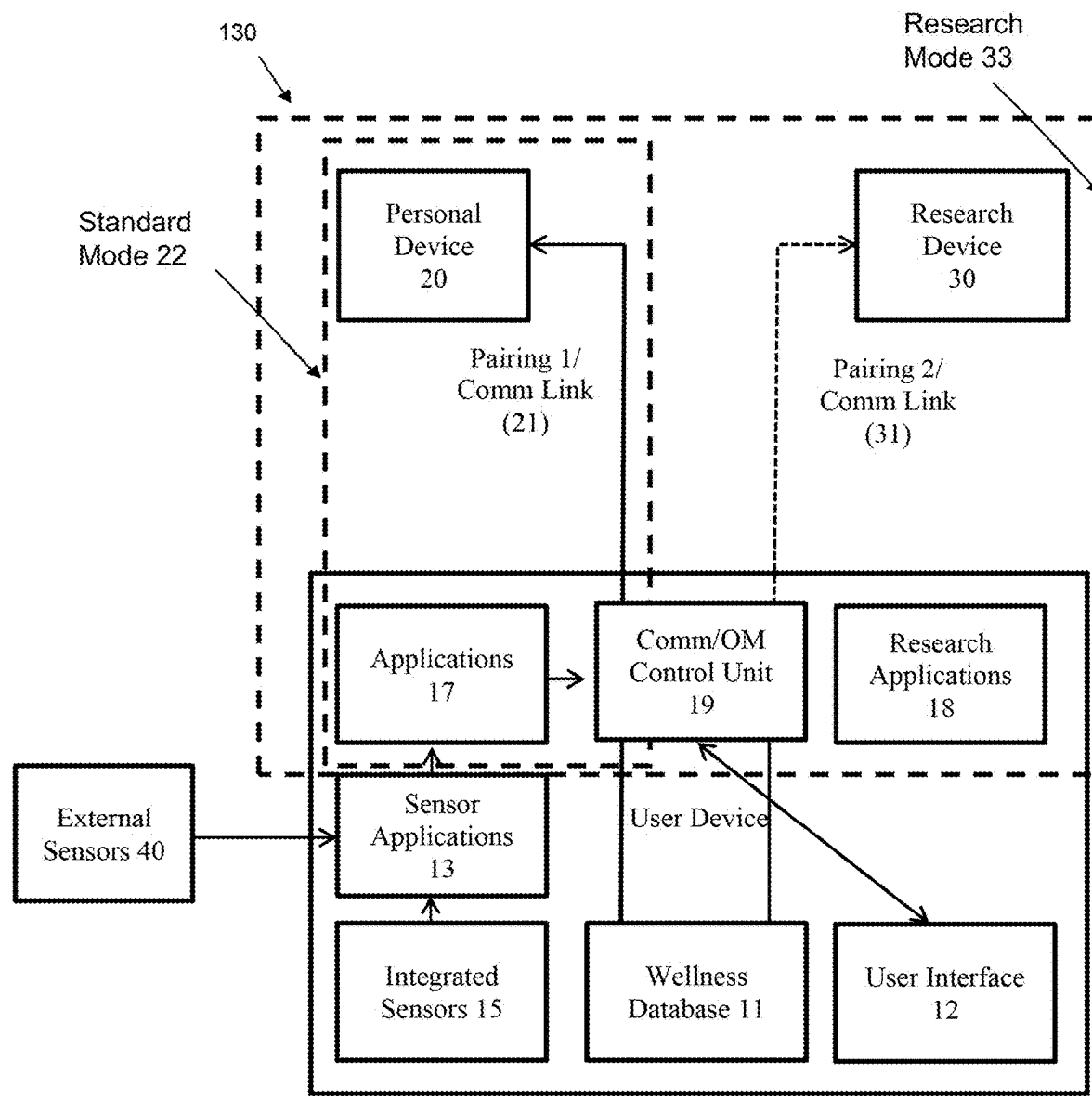
FIG. 7 is a schematic of an example system for facilitating research in accordance with some embodiments.

FIG. 7 illustrates a schematic of a wearable sensor device 10 having a standard operating mode 23, in which the device performs similar to that of a conventional wearable device having a single pairing, and a research operating mode 33, in which the wearable device can perform a first pairing operation with a first computing device 20 of the user or a second pairing operation with a second computing device 30 of a researcher. Such a research mode may include any of the features described herein useful for research. As shown, wearable device 10 includes much the same elements as those depicted in the device of FIGS. 5-6, except the control unit is configured with a standard operating mode and a research operating mode, which a user can switch between via a user input received on the user interface 12.

In one aspect, the research mode allows for customization or disabling of certain non-research application for the purposed of making additional resources available for research related activity, such as by reducing processor overhead, power consumption and network traffic.

In another aspect, wearable sensor device 10 may include a location feature that provides a locating output in response to a locating request received from a research computing device paired with the wearable device 10. Since in some embodiments, multiple wearable devices can be paired with a single companion, being able to locate and select which device or research participant can be difficult, particularly in a research study having a large number of participants. In some embodiments, the locating feature is adapted to allow a researcher to readily locate a subject by using a companion device or web based application to request the locating output from the wearable sensor device of the subject, for example an audible beep, to assist the researcher in locating the subject. In some embodiments, a common web front-end can be used in order to give multiple researchers access to the same health data and wearable devices.

In yet another aspect, the wearable sensor device 10 includes a user interface that indicates a mode status to the user. Communication unit may also output an indicator of status to the researching computing device, for exampling indicating on a user interface of the research computing device that a particular wearable computing device is in the research mode. For example, in response to a request received from a research computing device 30 to locate certain subject and/or groups of subjects, the subject's wearable devices 10 may output an indicator, which may be any of an audible, visual or tactile output.

In one aspect, the wearable devices may include a "bumping" feature that allows subject ID credentials to be automatically transferred from one wearable device to another, thereby enabling rapid swapping out of wearable device for a given subject when one of the devices needs to be repaired or exchanged, thereby allowing for near continuous service or monitoring of the subject provided by the wearable devices during the research study.

IV. Example Methods

In another aspect, the wearable device can be configured with multiple modes of operation to facilitate any of the pairing configurations described herein, communication of health information to a research device or to facilitate collection of data during research. FIGS. 13-14 illustrate example methods of facilitating research using a wearable computing device in accordance with embodiments of the invention.

Figure 8:
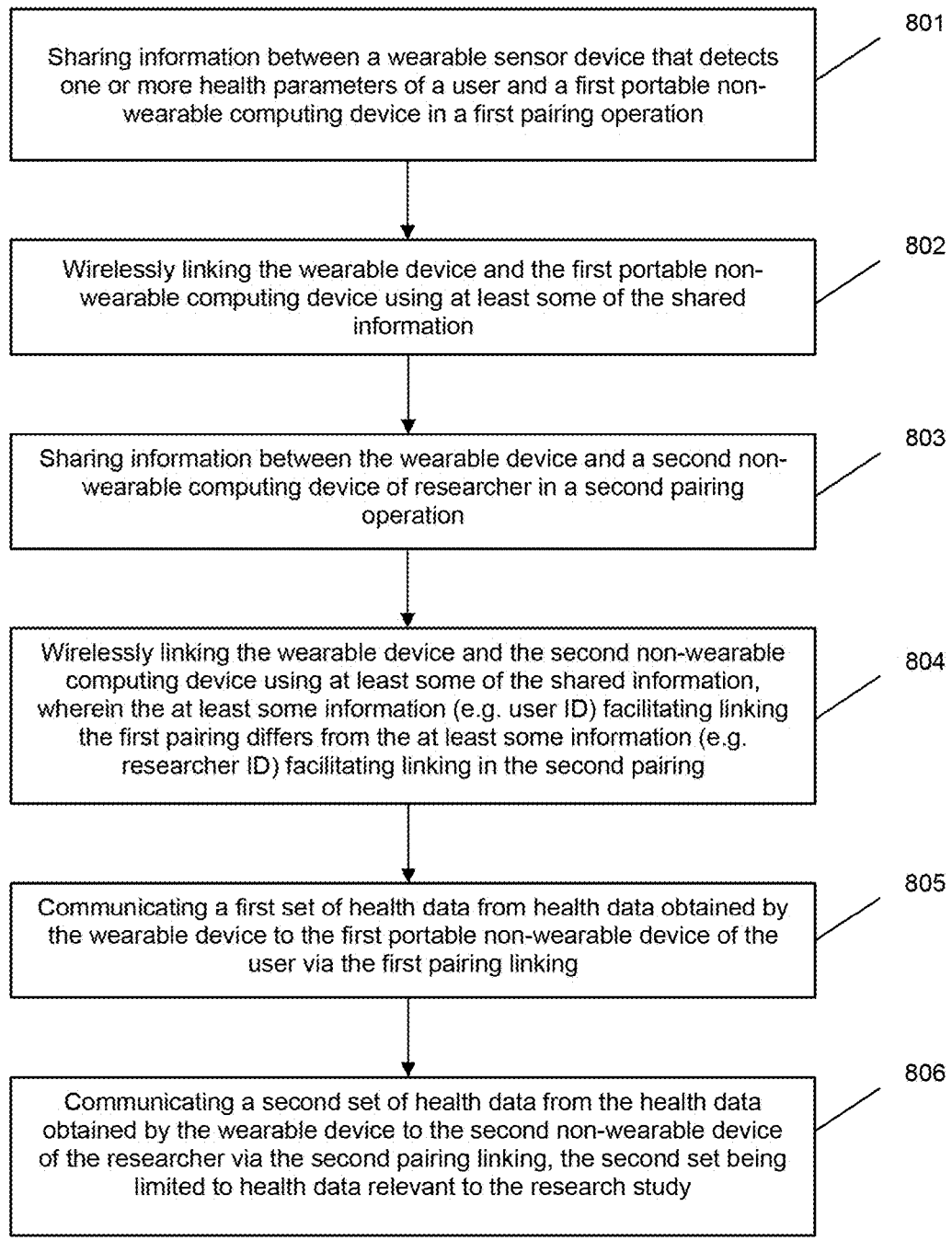
FIG. 8 is a flowchart illustrating an example method for facilitating health research using a wearable device in accordance with some embodiments.

FIG. 8 depicts a method for facilitating research comprising steps of: sharing information between a wearable sensor device that detects one or more health parameters of a user and a first portable non-wearable computing device in a first pairing operation 801; wirelessly linking the wearable device and the first portable non-wearable computing device using at least some of the shared information 802; sharing information between the wearable device and a second non-wearable computing device of researcher in a second pairing operation 803, such as in an encryption handshake; and wirelessly linking the wearable device and the second non-wearable computing device using at least some of the shared information, wherein the at least some information (e.g. user ID) facilitating linking the first pairing differs from the at least some information (e.g. researcher ID) facilitating linking in the second pairing 804. Once paired, the method further includes: communicating a first set of health data from health data obtained by the wearable device to the first portable non-wearable device of the user via the first pairing linking 805; and communicating a second set of health data from the health data obtained by the wearable device to the second non-wearable device of the researcher via the second pairing linking, the second set being limited to health data relevant to the research study 806.

Figure 9:
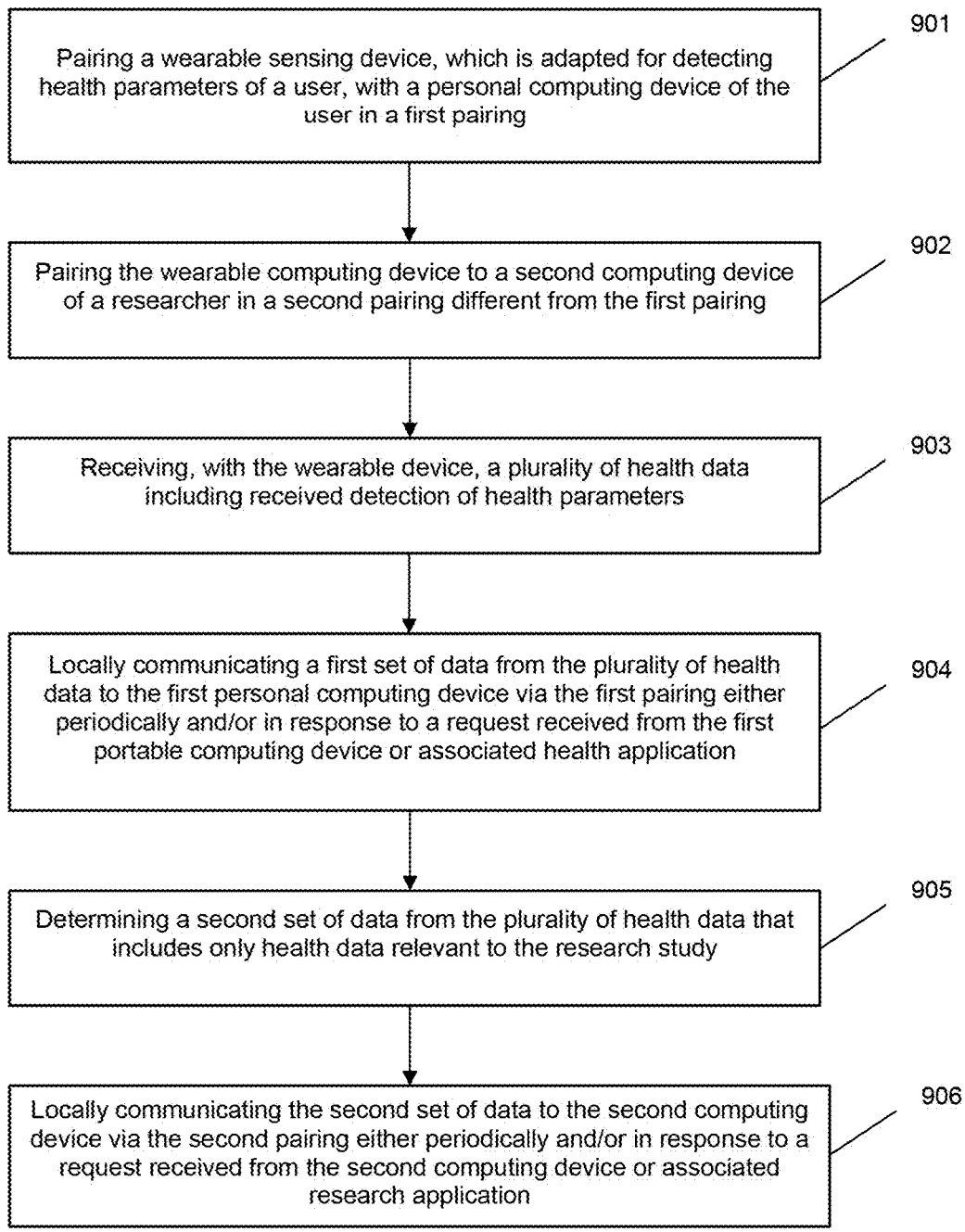
FIG. 9 is a flowchart illustrating an example method for facilitating health research using a wearable device in accordance with some embodiments.

FIG. 9 depicts a method for facilitating research that includes steps of: pairing a wearable sensing device, which is adapted for detecting health parameters of a user, with a personal computing device of the user in a first pairing 901; pairing the wearable computing device to a second computing device of a researcher in a second pairing different from the first pairing 902; receiving, with the wearable device, a plurality of health data including received detection of health parameters 903; locally communicating a first set of data from the plurality of health data to the first personal computing device via the first pairing either periodically and/or in response to a request received from the first portable computing device or associated health application 904; determining a second set of data from the plurality of health data that includes only health data relevant to the research study 905; and locally communicating the second set of data to the second computing device via the second pairing either periodically and/or in response to a request received from the second computing device or associated research application 906.

Figure 10:
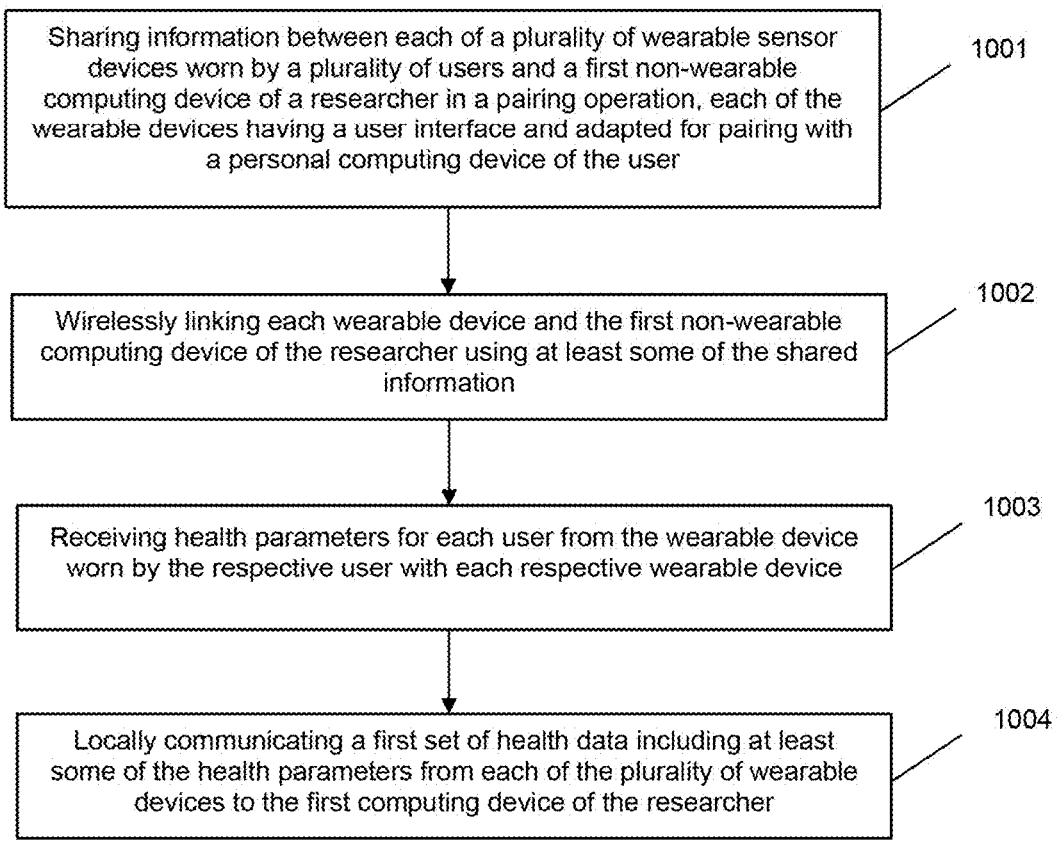
FIG. 10 is a flowchart illustrating an example method for facilitating health research using a wearable device in accordance with some embodiments.

FIG. 10 depicts a method for facilitating research that includes steps of: sharing information between each of a plurality of wearable sensor devices worn by a plurality of users and a first non-wearable computing device of a researcher in a pairing operation, each of the wearable devices having a user interface and adapted for pairing with a personal computing device of the user 1001; wirelessly linking each wearable device and the first non-wearable computing device of the researcher using at least some of the shared information 1002; receiving health parameters for each user from the wearable device worn by the respective user with each respective wearable device 1003; and locally communicating a first set of health data including at least some of the health parameters from each of the plurality of wearable devices to the first computing device of the researcher 1004.

Figure 11:
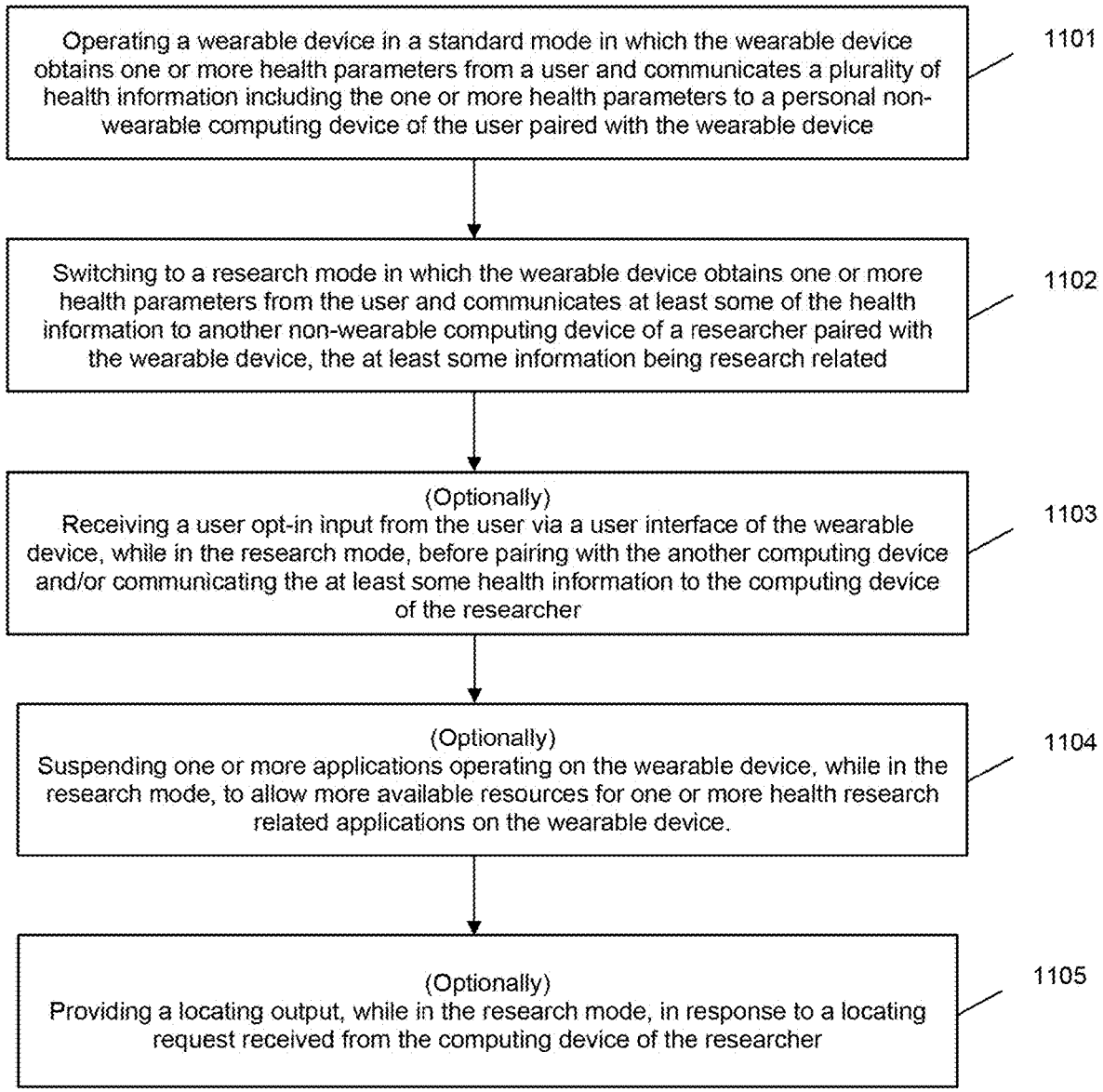
FIG. 11 is a flowchart illustrating an example method for facilitating health research using a wearable device in accordance with some embodiments.

FIG. 11 depicts a method for facilitating research that includes steps of: operating a wearable device in a standard mode in which the wearable device obtains one or more health parameters from a user and communicates a plurality of health information including the one or more health parameters to a personal non-wearable computing device of the user paired with the wearable device 1101; and switching to a research mode in which the wearable device obtains one or more health parameters from the user and communicates at least some of the health information to another non-wearable computing device of a researcher paired with the wearable device, the at least some information being research related 1102. In some embodiments, the method includes receiving a user opt-in input from the user via a user interface of the wearable device, while in the research mode, before pairing with the another computing device and/or communicating the at least some health information to the computing device of the researcher 1103. In other embodiments, the method further can further include suspending one or more applications operating on the wearable device, while in the research mode, to allow more available resources for one or more health research related applications on the wearable device 1104. In still other embodiments, the method can further include providing a locating output, while in the research mode, in response to a locating request received from the computing device of the researcher 1105.

Illustrative methods and systems for managing user device connections are described above. Some or all of these systems and methods may, but need not, be implemented at least partially by architectures such as those shown at least in FIGS. 1-14 above. While many of the embodiments are described above with reference to personal and/or health-related information, it should be understood any type of user information or non-user information may be managed using these techniques. Further, in the foregoing description, various non-limiting examples were described. For purposes of explanation, specific configurations and details are set forth in order to provide a thorough understanding of the examples. It is appreciated that the above examples may be practiced without certain specific details and that well-known features were sometimes omitted or simplified in order not to obscure the example being described.

The various embodiments further can be implemented in a wide variety of operating environments, which in some cases can include one or more user computers, computing devices or processing devices which can be used to operate any of a number of applications. User devices (e.g., client devices) can include any type of general purpose personal computer such as, but not limited to, desktop or laptop computers running a standard operating system, as well as cellular, wireless, and/or handheld devices running mobile software and capable of supporting a number of networking and messaging protocols. These devices can also include other electronic devices, such as dummy terminals, thin-clients, gaming systems, or other devices capable of communicating via a network.

Most embodiments utilize at least one network that would be familiar to those skilled in the art for supporting communications using any of a variety of commercially-available protocols, such as TCP/IP, OSI, FTP, UPnP, NFS, and CIFS. The network can be, for example, a local area network, a wide-area network, a virtual private network, the Internet, an intranet, an extranet, a public switched telephone network, an infrared network, a wireless network, and any combination thereof.

The environment can include a variety of data stores and other memory and storage media as discussed above. These can reside in a variety of locations, such as on a storage medium local to (and/or resident in) one or more of the computers. Alternatively, the memory can be remote from any or all of the computers across the network. In a particular set of embodiments, the information may reside in a storage-area network (SAN) familiar to those skilled in the art. Similarly, any necessary files for performing the functions attributed to the computers, servers or other network devices may be stored locally and/or remotely, as desired.

The system and various devices may also include one or more software applications, modules, services, or other elements located within at least one working memory device, including an operating system and application programs, such as a client application or browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

What is claimed is:

1. A wearable device, the device comprising:
   one or more sensors adapted for detecting one or more health parameters of a user when the device is worn by the user;
   a wireless communication link adapted for near field/local communication with one or more computing devices including communications for pairing with the one or more computing devices and communications for transmitting one or more health parameters to the one or more computing devices;
   user interface for receiving user input and for outputting information regarding the one or more detected health parameters to the user; and
   a control unit for controlling operation of the wearable device,
   wherein the wearable device is configured to perform:
   a first pairing for standard operation that pairs and communicates with at least one computing device by utilizing a user ID when within a wireless communication range of the at least one computing device to facilitate communication of a first plurality of health data comprising detections of the one or more health parameters obtained from the one or more sensors, and
   a second pairing for health research that pairs and communicates by secure authenticated communication with at least one other computing device by utilizing a third party ID, which is associated with health research in which the user is a participant to facilitate communication of a second plurality of health data that is relevant to the health research, wherein the communication of the second plurality of health data is authorized for release by the user.

2. The wearable device of claim 1, wherein the first pairing and the second pairing are maintained concurrently to facilitate both standard operation and health research.

3. The wearable device of claim 1, wherein the third party ID is associated with one or more health researchers associated with the health research.

4. The wearable device of claim 1, wherein:
   through the first pairing, the device communicates health research data and non-research data with the at least one computing device associated with the user ID, and
   through the second pairing, the device communicates only research data to the at least one other computing device associated with the third party ID.

5. The wearable device of claim 1, wherein the first pairing and second pairing each utilize a single user ID stored on the wearable device, wherein the first pairing utilizes the user ID associated with the user wearing the wearable device and the second pairing utilizes the third party ID associated with the health research in which the user is a participant.

6. The wearable device of claim 1, wherein the at least one other computing device comprises multiple computing devices associated with the third party ID, and wherein the wearable device communicates at least some of the one or more health parameters of the second plurality of health data to any of the multiple computing devices associated with the third party ID.

7. The wearable device of claim 1, wherein the device is configured such that communication of the second plurality of health data requires a separate opt-in and/or authorization from the user received via the user input of the wearable device.

8. A system comprising:
   a device wearable on a wrist of a user including:
      one or more sensors adapted to detect one or more health parameters of the user when the device is worn;
      a user interface for presenting information regarding the one or more health parameters to the user; and
      a wireless communication unit adapted to for pairing and local communication with multiple companion computing devices;
   a first portable non-wearable computing device of the user adapted to pair with the wearable device in a first pairing configured for standard operation of the wearable device so as to allow subsequent exchanges of a first plurality of health data to the first computing device, the first plurality of health data including the one or more health parameters detected by the one or more sensors, wherein the first pairing utilize a first user ID associated with the user; and
   a second non-wearable computing device of a third party that is paired with the wearable device in a second pairing that is configured for health research to allow subsequent exchanges of a second plurality health data to the second computing device, the second plurality of health data including at least some of the one or more health parameters detected by the one or more sensors, wherein the second pairing utilizes a third party ID associated with health research in which the user is a participant.

9. The system of claim 8, wherein the third party ID is associated with one or more health researchers associated with health research in which the user is a participant.

10. The system of claim 8, wherein each of the first and second pairings utilize a single user ID stored on the wearable device, the first pairing utilizing the first user ID associated with the user and the second pairing utilizing the third party ID associated with health research.

11. The system of claim 8, wherein the first and second computing devices are concurrently paired with the wearable device.

12. The system of claim 8, wherein the second plurality of health data is a subset of the first plurality of health data that is associated with a research study.

13. The system of claim 8, wherein the user ID is not determinable from the second pairing or third party ID by the second computing device.

14. The system of claim 8, wherein the first pairing utilizes a first authentication authorizing communication of the first plurality of health data and the second pairing utilizes a second authentication authorizing communication of the second plurality of health data.

15. The system of claim 8, wherein the system is configured such that authorizing communication further includes a researcher requesting for the second plurality of health data from the second computing device and a user opt-in approval.

16. The system of claim 8, wherein the second pairing is configured to require user opt-in and/or user confirmation received on the wearable device before completing the second pairing between the wearable device and the second computing device.

17. The system of claim 8, wherein each of the first and second pairings are configured such that subsequent communication between respective paired devices are pre-authenticated.

18. A method of facilitating a research study, the method comprising:
   obtaining health data parameters of a user with a wearable device worn by the user, the health data parameters measured by one or more sensors associated with the wearable device;
   establishing a first pairing between the wearable device worn by the user and a first computing device that is portable and non-wearable, wherein the first pairing is configured for standard operation of the wearable device and utilizes a user ID of the user stored thereon;
   communicating a first plurality of health data parameters between the wearable device worn by the user and the first computing device of the user through the first pairing to facilitate personal use of the wearable device by the user;
   establishing a second pairing between the wearable device and a second computing device that is non-wearable, wherein the second pairing is configured for health research and utilizes a third party ID associated with health research in which the user is a participant; and
   communicating a second plurality of health data parameters that is relevant to the health research to the second computing device through the second pairing to facilitate health research.

19. The method of claim 18, wherein the second plurality of health data is a subset of the first plurality of health data that includes only research related health data.

20. The method of claim 18, wherein the first and second pairings are concurrently maintained to facilitate use of the wearable device for both standard operation and for health research.

* * * * *